United States Patent
Kroll et al.

[11] Patent Number: 6,112,118
[45] Date of Patent: *Aug. 29, 2000

[54] IMPLANTABLE CARDIOVERTER DEFIBRILLATOR WITH SLEW RATE LIMITING

[76] Inventors: Mark W. Kroll, 13011 Brenwood Trail, Minnetonka, Minn. 55343; Joseph S. Perttu, 790 Santa Vera Dr., Chanhassen, Minn. 55317

[ * ] Notice: This patent is subject to a terminal disclaimer.

[21] Appl. No.: 08/896,311

[22] Filed: Jun. 28, 1997

Related U.S. Application Data

[63] Continuation of application No. 08/615,516, Mar. 12, 1996, Pat. No. 5,645,572.

[51] Int. Cl.[7] .................................................. A61N 1/39
[52] U.S. Cl. ................................................................ 607/5
[58] Field of Search .............................................. 607/5, 4

[56] References Cited

U.S. PATENT DOCUMENTS

| | | | |
|---|---|---|---|
| 3,718,142 | 2/1973 | Mulier | 607/36 |
| 4,006,748 | 2/1977 | Schulman | 607/36 |
| 4,372,324 | 2/1983 | Rockwell | 607/8 |
| 5,170,806 | 12/1992 | Colen | 128/901 |
| 5,496,349 | 3/1996 | Campbell et al. | 607/5 |
| 5,601,607 | 2/1997 | Adams | 607/5 |
| 5,626,619 | 5/1997 | Jacobson et al. | 607/5 |

Primary Examiner—William E. Kamm
Assistant Examiner—Kennedy J. Schaetzle
Attorney, Agent, or Firm—Brad Pedersen

[57] ABSTRACT

The present invention is a pectorally implantable defibrillation system for delivering at least one electrical cardioversion/defibrillation countershock. The system has a housing designed to be implanted in a human patient, wherein the housing has an outer shell and an inner cavity. Pulse generating circuitry is positioned within the cavity for generating the at least one countershock. Circuitry is also positioned within the cavity to control delivery of the at least one countershock. A slew rate limiting circuit is connected between the pulse generating circuitry and one of a plurality of implantable electrodes so as to reduce a slew rate of the electrical countershock. Preferably, one of the implantable electrodes is the housing.

6 Claims, 3 Drawing Sheets

IMPLANTABLE CARDIOVERTER DEFIBRILLATOR WITH SLEW RATE LIMITING

This is a continuation of application Ser. No. 08/615,516 filed on Mar. 12, 1996, now U.S. Pat. No. 5 645,572.

RELATED APPLICATIONS

The present invention is related to co-pending U.S. patent application entitled "SHIELD FOR IMPLANTABLE CARDIOVERTER DEFIBRILLATOR", Ser. No. 08/486,759, filed Jun. 7, 1995 which is assigned to the assignee of the present invention, the disclosure of which is herein incorporated by reference in this application.

FIELD OF THE INVENTION

The invention relates to implantable cardioverter defibrillators, and more particularly, to implantable cardioverter defibrillators having internal circuitry subject to adverse capacitive coupling effects.

BACKGROUND OF THE INVENTION

Cardiac muscle fibrillation is the rapid and asynchronous contraction of individual muscle fibers in the heart. The result is a slightly quivering and non-functional heart muscle. When fibrillation occurs within the lower chambers of the heart or ventricles, blood flow ceases and, if not corrected within minutes, death of the patient will result. Fibrillation occurring only in the upper chambers of heart or atria results in a diminution of cardiac output that may be symptomatic to the patient. Other forms of cardiac dysrhythmia include ventricular or supraventricular tachycardia, which are very rapid orgailized/synchronous muscle fiber contractions that impair cardiac output to lesser or greater degrees dependent on cardiac refill times and preload pressures.

Implantable cardiovertex and defibrillator (ICD) systems attempt to treat of cardiac dysrhythmias by passing through the heart muscle a cardioversion or defibrillation countershock, depending on the type of cardiac dysrhythmia diagnosed. An objective of the cardioversion or defibrillation countershock is to immerse as much of the myocardium as possible within the electrical field generated by the countershock. The countershock is a truncated capacitive discharge of electrical energy that generally ranges from 0.1 to 5.0 joules for cardioversion and from 5 to 40 joules for defibrillation of the ventricles.

U.S. Pat. No. 4,774,950, the disclosure of which is incorporated herein by reference, discloses an embodiment of an abdominally implanted ICD. U.S. Pat. No. 5,405,363, the disclosure of which is also incorporated herein by reference, describes embodiments of a pectorally implanted ICD.

Conventional abdominally implanted ICDs include a metal housing that floats with respect to the internal electronic circuitry. The housing is not physically secured to the internal electronics and is tied to the battery ground through a high impedance, typically 200K ohms. This is desirable to prevent the housing from acting as an electrode and thereby siphoning off current that should flow between the two defibrillation electrodes. Preventing the housing from acting as an electrode at an abdominal location is especially desirable, to avoid diverting current from the heart. Even though the housing is essentially floating, the housing acts as a shield against electromagnetic interference and protects the internal electronic circuitry from picking up induced pulses from stray electromagnetic fields.

Unlike abdominally implanted ICD's, pectorally implanted ICD's, such as described in U.S. Pat. No. 5,405, 363, typically use the housing as one of the electrodes. When the housing is used as an electrode, implanting the housing in the pectoral region on the patient's left side and inserting a transvenous electrode into the patient's right ventricle will cause the defibrillation current to be directed along a very desirable vector. This results in a lower defibrillation threshold, that is, a lower minimum energy to produce successful defibrillation.

A common approach to delivering shocks with an ICD is to divide the shock into more than one phase. With biphasic waveforms, the polarity of the second phase is opposite to that of the first phase. It has been demonstrated that many biphasic waveforms can successfully defibrillate with consistently lower voltage and energy requirements than monophasic waveforms of the same duration. With biphasic waveforms the two electrodes of the defibrillator change polarities in mid-pulse.

When using a pectorally implanted housing as an electrode for biphasic-waveform shocks, the housing must be switched from one polarity of the output capacitor to the opposite polarity. In this case, the housing of the device cannot serve as an electrode simply by tying the housing to one of the battery electrodes, as it could be done for a monophasic pulse. When the housing is configured as an electrode for pectorally implanted ICD delivering a biphasic waveform, the housing acts as a large, first plate of a capacitor, and the other conductors in the circuitry of the ICD act as a second plate of the capacitor. When the housing voltage suddenly changes, voltages and currents are induced on nearby conductors. These induced currents and voltages potentially can be of sufficient magnitude so as to introduce unwanted logic signals or switching signals in the circuitry of the ICD, which have the possibility of causing circuit malfunctions and consequent harm to the patient.

For circuits with conductors having significant length, or lying adjacent to the housing, this kind of capacitive coupling effect is magnified. Such conductors are common in ICDs having interconnect wiring between various parts of the circuit, for example. These conductors often are in a medium known as a "flex tape," wherein conductive paths are printed on a flexible dielectric film that is wrapped, folded and bent to reach various points of the circuit to which connections must be made. Often, the most convenient route for the flex tape to reach these various points is around the outside of the electronics core, that is, near the inside surface of the housing thereby increasing the likelihood of undesirable capacitive coupling.

One way to address the problem of noise imparted onto the low voltage circuitry in a pectorally implanted ICD is to shield the circuitry so as to reduce the capacitive coupling between the housing and the circuitry. This is described in U.S. Ser. No. 08/486,759, filed Jun. 7, 1995, which, as stated above, is assigned to the assignee of the present invention and which has been incorporated by reference. This solution has the drawback of potentially increasing the total volume of the internal circuitry of the ICD and thereby limiting the overall size of the device. The shield current itself can inductively couple stray signals into the circuitry due to its imperfect conductivity and grounding.

As ICDs become smaller, especially pectorally implanted ICDs, the interconnect conductors and electronics are positioned nearer to the inside housing surface of the device.

When the housing of the ICD is used as a switchable electrode, it is no longer possible to couple the housing to ground, for example, to allow the housing to serve as a capacitor coupling shield. Consequently, capacitive coupling problems that have not been experienced in the past are impacting the design and operation of new ICDs. These unanticipated capacitive coupling problems limit the miniaturization and effective operation of such devices.

SUMMARY OF THE INVENTION

To address these and other problems, a pectorally implantable defibrillation system for delivering at least one electrical cardioversion/defibrillation countershock is described. The system has a housing designed to be implanted in a human patient, wherein the housing has an outer shell and an inner cavity. Pulse generating circuitry is positioned within the cavity for generating the at least one countershock. Circuitry is also positioned within the cavity to control delivery of the at least one countershock. At least one surface of the outer shell is preferably electrically conductive to form an electrode for the system. A slew rate limiting circuit is connected between the pulse generating circuitry and the electrode. The slew rate limiting circuitry reduces the rate of change of the voltage at the electrode. By reducing the rate of change of the voltage, a slew rate of the electrical countershock is reduced.

BRIEF DESCRIPTION OF THE DRAWINGS

FIG. 5 is a simplified schematic of an output circuit according to a third embodiment of the present invention.

FIG. 6 is a simplified schematic of an output circuit according to a fourth embodiment of the present invention.

DETAILED DESCRIPTION OF PREFERRED EMBODIMENTS

The amount of current coupled to the low voltage circuitry inside the housing of an ICD is proportional to the product of the capacitive coupling value and the slew rate of the voltage. The slew rate of the voltage (dv/dt) is the number of volts per second change in the voltage. For representative values of 100 pF for the capacitive coupling and $10^{10}$ V/µs for the slew rate, the current induced on the low voltage circuitry is 1 ampere overall of the circuitry but which local portbus are sufficient to disrupt the low amplitude signals typically used within an ICD.

Figure 1:
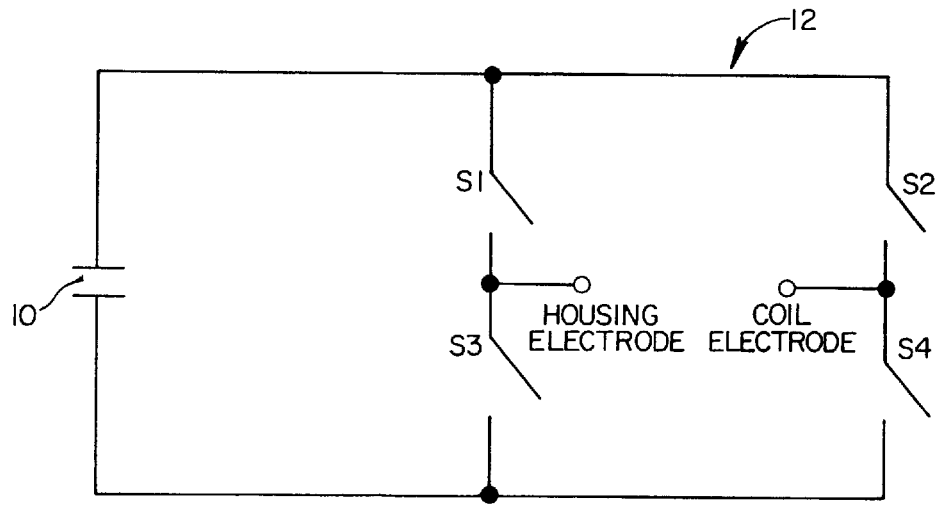
FIG. 1 is a simplified schematic of a basic output circuit of a known implantable cardioverter and defibrillator (ICD).
Figure 2:
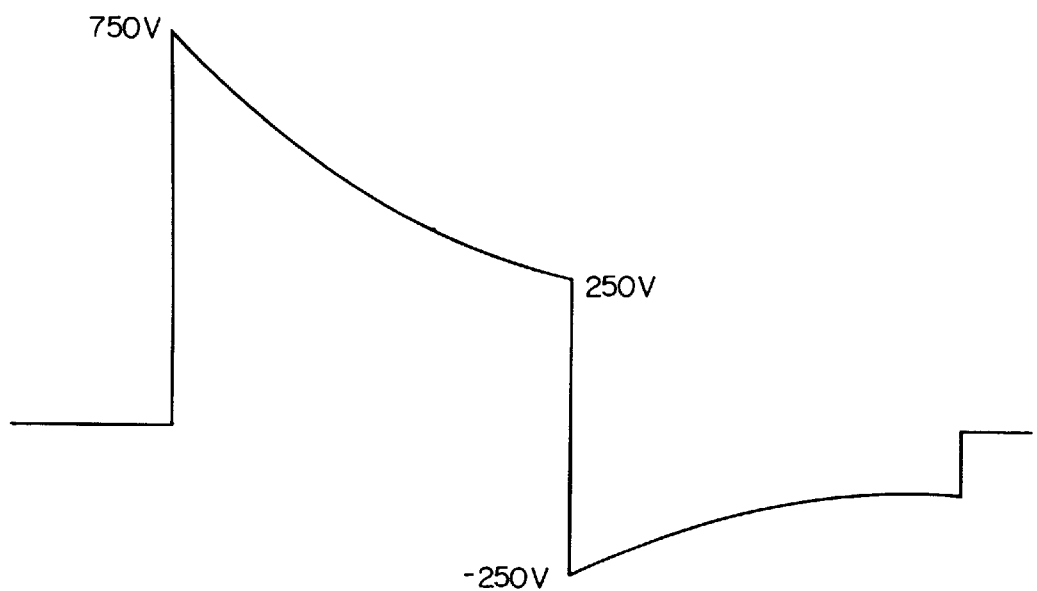
FIG. 2 is the waveform generated from the circuit in FIG. 1.

FIG. 1 illustrates a simplified schematic of a basic output circuit of a kown ICD. A high voltage capacitor 10 is illustrated connected to a 4 switch H-Bridge 12. Switches S1 and S3 deliver connections to an ICD housing 14 while switches S2 and S4 deliver connections to a coil 16. In a typical operation, capacitor 10 is charged up to its full voltage, typically 750 V. Switches S1 and S4 are then turned on to pass current through the heart in one direction. Shortly thereafter, S1 and S4 are turned off and switches S2 and S3 are turned on to pass current in the reverse direction. This generates the waveform illustrated in FIG. 2. The initial voltage on housing 14 is 750 V, which decays to 250 V over a period of approximately 4 ms. With the switching of the polarity, a negative 250 V is delivered which then decays to a negative 150 V. The problem of an excessive dv/dt can be readily seen here.

The present invention is a slew rate limiting circuit. The goal of the present invention is to reduce the slew rate seen at the electrode to somewhere in the range of 50 to 1,000 V/µS.

Figure 3:
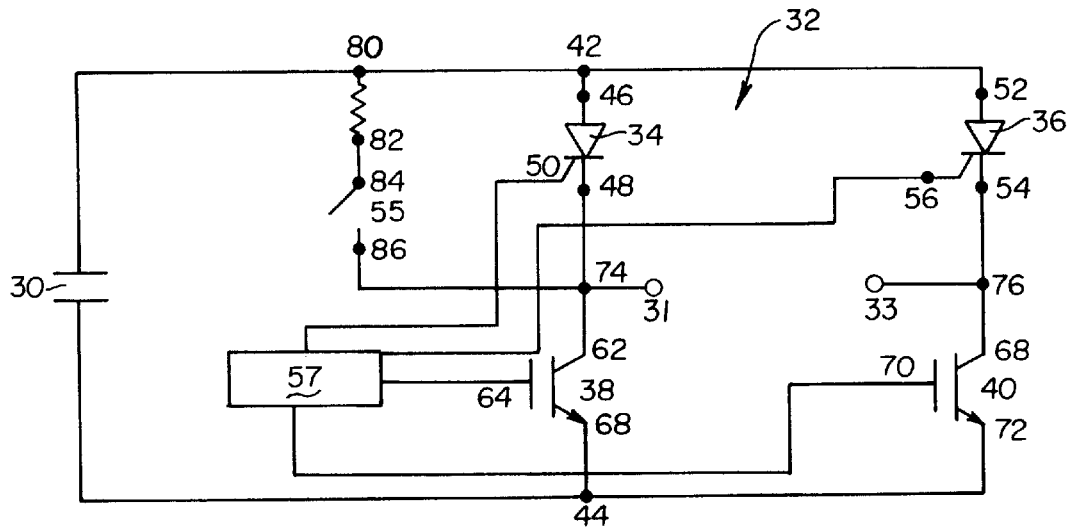
FIG. 3 is a simplified schematic of an output circuit according to a first embodiment of the present invention.

FIG. 3 illustrates a first embodiment of the present invention. A high voltage capacitor 30 is illustrated in FIG. 3. It should be noted that capacitor 30 need not be a single capacitor but may be a combinatorial network of capacitors. It should also be noted that, the pulse generator circuitry for generating a charge on capacitor 30 is not illustrated. A four switch H-bridge 32 is illustrated connected to capacitor 30. The switches of the H-bridge deliver connections to a housing electrode 31 and a coil electrode 33. H-bridge 32 is shown with the four switches in their common realization. Specifically, H-bridge 32 is shown having silicon control rectifiers (SCRs) 34, 36 and insulated gate bipolar transistors (IGBTs) 38, 40 as the switching elements. SCR 34 has an anode 36, a cathode 38 and a gate 50. Likewise, SCR 36 has an anode 52, a cathode 54 and a gate 56.

IGBTs combine the attributes of a metal-oxide-semiconductor-field-effect-transistor (MOSFET) and a bipolar junction transistor (BJT). IGBT 38 includes a collector 62, a gate 64 and an emitter 66. IGBT 40 has a collector 68, a gate 70 and an emitter 72. The anodes of SCRs 34, 36 are both connected to a node 42. Cathode 48 of SCR 34 is connected to a node 74 which is also connected to housing electrode 31. Cathode 54 of SCR 36 is connected to a node 76 which is also connected to coil electrode 33. Gates 50 and 56 of SCRs 34, 36, respectively are illustrated connected to a signal control block 57. These gate terminals are the control device for turning on and off the SCRs. For ease of understanding the present invention, signal control block 57 is being illustrated only generally. Likewise, gates 64, 70 of IGBTs 38, 40, respectively, control the operation of the IGBTs. They too are connected to signal control block 57. Collector 62 of IGBT 38 is connected to node 74 while emitter 66 is connected to a node 44. Collector 68 of IGBT 40 is connected to node 76 while emitter 72 is also connected to node 44.

The invention for limiting the slew rate at housing electrode 31 is embodied by adding a resistor R1 and a switch S5. Resistor R1 has a first end 80 and a second end 82. First end 80 of R1 is connected to node 42 while second end 82 of resistor R1 is connected to a first end 84 of switch S5. A second end 86 of switch S5 is connected to node 74.

In operation, capacitor 30 is charged to its full voltage, typically 750 volts. Shortly before a positive voltage is to be applied to housing electrode 31, switch S5 is closed, or turned on. This then charges housing electrode 31 to the maximum voltage on capacitor 30. The slew rate is limited by resistor R1. As stated above, inside the housing, very close to housing electrode 31 is the low voltage circuitry. There is a coupling capacitance between housing electrode 31 and the low voltage circuitry on the order of 100 picofarads. Resistor R1 in the preferred embodiment has a value of 10K ohms, but greater or lesser values could be used without departing from the spirit or scope of the invention.

The current coupled to the circuitry inside the housing can be calculated using the following equation:

$$I = V/R$$

As previously stated, the slew rate can be calculated by the following equation:

$$dv/dt = I/C$$

Using the values of 750 volts, 10K ohms, and 100 pf, the slew rate at housing electrode 31 will be 750 V/µS, which is well below the level at which the low voltage signals may be disrupted. As stated above, the goal is to get in the range of 50 to 1,000 V/µS for the slew rate. Once housing electrode 31 has been charged through resistor R1 and switch S5, SCR 34 and IGBT 40 are turned on to pass current through the heart in one direction. Shortly thereafter, SCR 34 and IGBT 40 are turned off and SCR 36 and IGBT 38 are turned on to pass current in the reverse direction.

Figure 4:
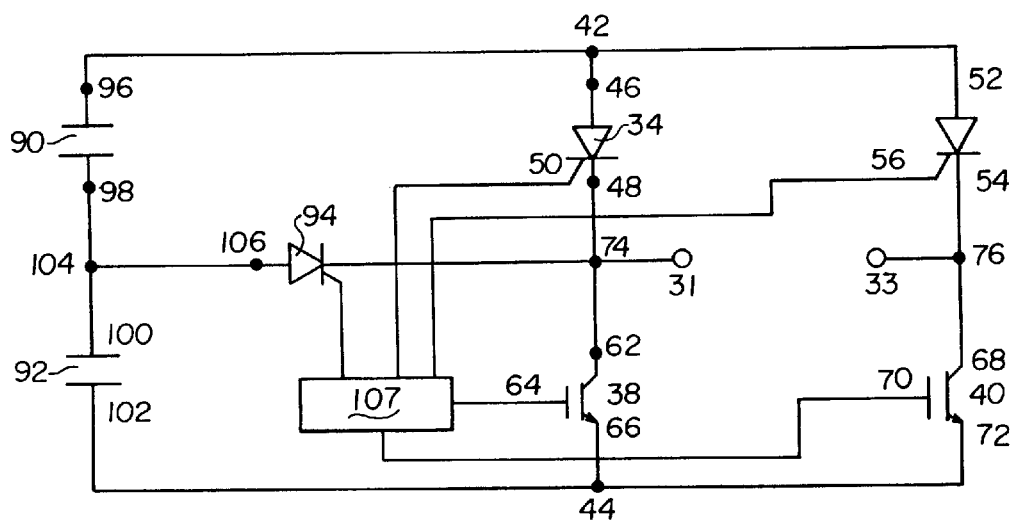
FIG. 4 is a simplified schematic of an output circuit according to a second embodiment of the present invention.

FIG. 4 illustrates a second embodiment of the present invention. The H-bridge configuration, the electrode housing and the coil electrode are the same in FIG. 4 as they were in FIG. 3 and therefore like elements are correspondingly identified. The invention for limiting the slew rate at housing electrode 31 is embodied by replacing capacitor 30 from FIG. 3 with a pair of photoflash capacitors 90, 92 and connecting a SCR 94 between the capacitors and housing electrode 31. Capacitor 90 has an upper plate 96 and a lower plate 98 and likewise, capacitor 92 has an upper plate 100 and a lower plate 102. Lower plate 98 of capacitor 90 is connected to upper plate 100 of capacitor 92 at a node 104. Upper plate 96 of capacitor 90 is connected to node 42 while lower plate 102 of capacitor 92 is connected to node 44. SCR 94 has an anode 106 which is connected to node 104 and a cathode which is connected to node 74. As with the previous circuit, a general signal control block 107 is illustrated which controls the operation of SCR 94.

In operation, capacitors 90, 92 are each charged to 375 Volts, to arrive at the total 750 Volts, as in FIG. 3. SCR 94 is then turned on, which allows housing electrode 31 to be pre-charged to half of the full voltage, before SCR 34 and IGBT 40 are turned on. This thus reduces the slew rate at the housing electrode by one half.

Figures 5, 6:
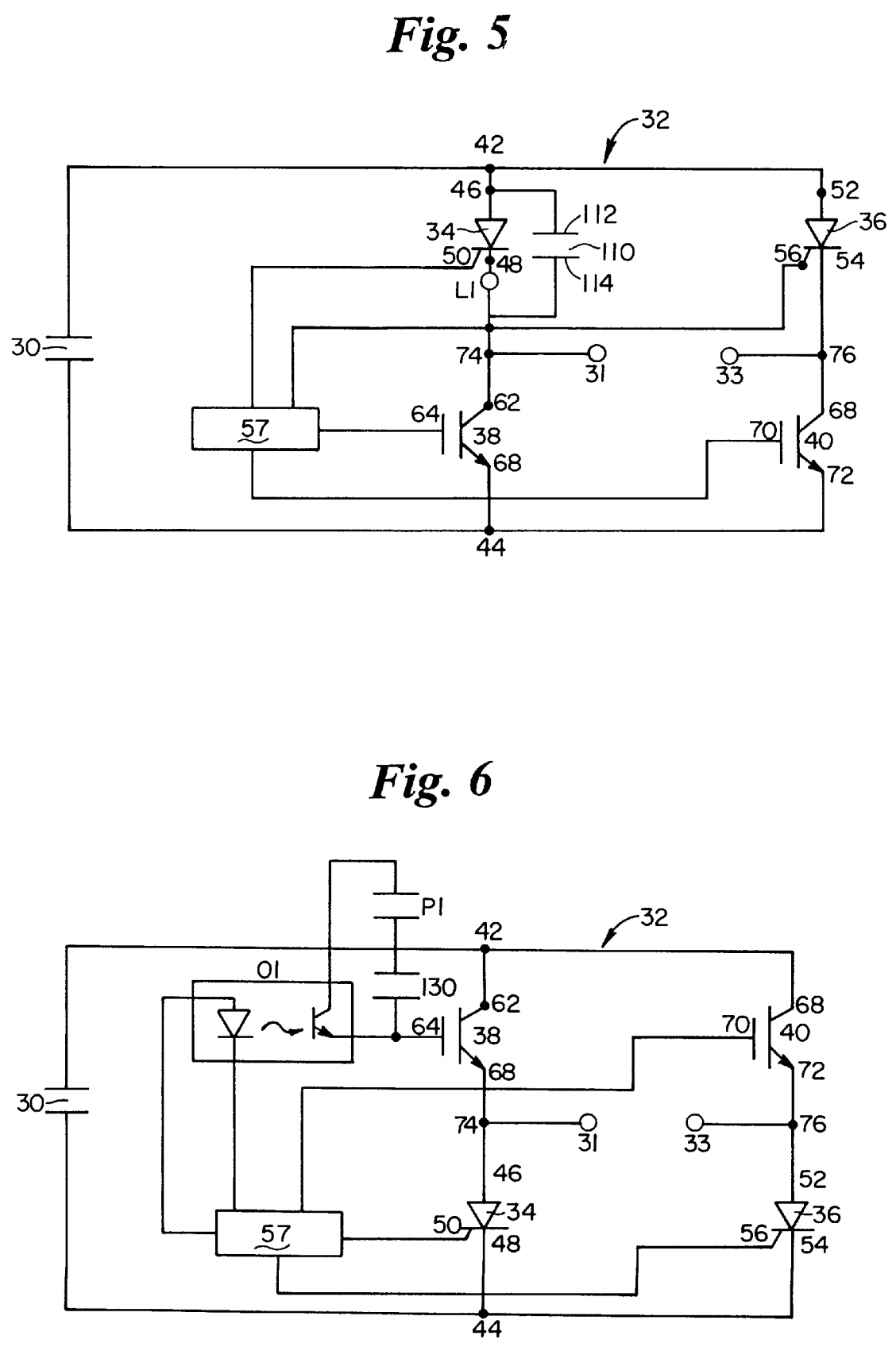

FIG. 5 illustrates a third embodiment of the present invention. The H-bridge configuration, the electrode housing and the coil electrode are again the same in FIG. 5 as they were in FIG. 3 and therefore like elements are correspondingly identified. The invention for limiting the slew rate at housing electrode 31 is embodied by connecting an inductor, such as a ferrite bead L1, to cathode 48 of SCR 34 and to node 74. Additionally, a shall capacitor 110, having an upper plate 112 and a lower plate 114, is coructed in parallel across SCR 34 and ferrite bead L1 such that upper plate 11 is connected to node 42 and lower plate 114 is connected to node 74. Capacitor 110 is on the order of 1 µf, but greater or lesser capacitive values may be chosen without departing from the spirit or scope of the invention. This type of arrangement is commonly referred to as a snubber.

In operation, with SCR 34 and IGBT 40 off, capacitor 110 will be charged to a large voltage potential. When SCR 34 and IGBT 40 turn on, SCR 43 causes capacitor 110 to discharge through the SCR before a full charge from capacitor 30 can be given to housing electrode 31. Ferrite bead L1 limits the rate of rise of the current. The operation of the ferrite bead and capacitor 110 significantly reduces the slew rate at the housing electrode. In this embodiment, there is a good chance that bead L1 may become saturated and lose its ability to restrict the rising current. Nevertheless, any limiting that is done before bead L1 saturates will still reduce the slew rate. It would also be possible to utilize either bead L1 or capacitor 110 alone to reduce the slew rate. It would furthermore be possible to connect lower plate 114 directly to node 44.

FIG. 6 illustrates a fourth embodiment for the present invention. The electrode housing and the coil electrode are the same in FIG. 6 as they were in FIG. 3 and therefore like elements are correspondingly identified. The H-bridge conlfiguration in FIG. 6 is reversed from that in the previous figures. In this case IGBTs 38, 40 are on the high side of H-bridge 32. Because IGBTs 38, 40 are more difficult to turn on than the SCRs, a special power supply circuit P1 has been provided, which gives voltages above those available from the maximum capacitor voltage. An optical isolator O1 is provided between the control circuit (not shown) and gate 64 of IGBT 38 for turning on the IGBT. The invention for limiting the slew rate at housing electrode 31 is embodied by connecting a capacitor 130 between power supply P1 and gate 64 of IGBT 38.

In operation the cap 130 limits the rate by which the voltage on gate 64 is allowed to rise. This, in turn, reduces the rate at which the IGBT 38 is turned on which, finally, reduces the dv/dt at housing electrode 31.

We claim:

1. An implantable defibrillation system for delivering at least one electrical countershock of greater than 0.5 joules to a plurality of implantable electrodes, the system comprising:

a housing of biocompatible material having an outer shell and an inner cavity;

pulse generating circuitry positioned in the cavity for generating the at least one countershock, the pulse generating circuitry including a high voltage output capacitor system connected to first, second, third and fourth switches, arranged in an H-bridge configuration such that a first implantable electrode is connected between the first and third switches and a second implantable electrode is connected between the second and fourth switches; and slew rate limiting circuitry comprising a resistor and a fifth switch connected in parallel with the first switch of the pulse generating circuitry to reduce the slew rate of an electrical countershock delivered from the output capacitor system.

2. An implantable defibrillation system for delivering at least one electrical countershock of greater than 0.5 joules to a plurality of implantable electrodes, the system comprising:

a housing of biocompatible material having an outer shell and an inner cavity:

pulse generating circuitry positioned in the cavity for generating the at least one countershock, the pulse generating circuitry including a high voltage output capacitor system having a first and second capacitor connected in series connected to first, second, third and fourth switches, arranged in an H-bridge configuration such that a first implantable electrode is connected between the first and third switches and a second implantable electrode is connected between the second and fourth switches; and slew rate limiting circuitry comprising a fifth switch having first and second ends wherein the first end connected at a junction of the first and second capacitors and the second end is connected to the first implantable electrode to reduce the slew rate of an electrical countershock delivered from the output capacitor system.

3. The system of claim 2 wherein the pulse generating circuitry further includes control circuitry to operate the H-bridge configuration to deliver the electrical countershock as a biphasic waveform.

4. The system of claim 1 wherein the pulse generating circuitry further includes control circuitry to operate the H-bridge configuration to deliver the electrical countershock as a biphasic waveform.

5. An implantable defibrillation system for delivering at least one electrical countershock of greater than 0.5 joules to a plurality of implantable electrodes, the system comprising:

a housing of biocompatible material having an outer shell and an inner cavity;

pulse generating circuitry positioned in the cavity for generating the at least one countershock, the pulse generating circuitry including a high voltage output capacitor system having connected to first, second, third and fourth switches, arranged in an H-bridge configuration such that a first implantable electrode is connected between the first and third switches and a second implantable electrode is connected between the second and fourth switches; and slew rate limiting circuitry comprising an inductor which is connected in series with the first switch to reduce the slew rate of an electrical countershock delivered from the output capacitor system.

6. The system of claim 5 wherein the pulse generating circuitry further includes control circuitry to operate the H-bridge configuration to deliver the electrical countershock as a biphasic waveform.

* * * * *